(12) United States Patent
Androsov et al.

(10) Patent No.: US 9,447,031 B2
(45) Date of Patent: Sep. 20, 2016

(54) COMPOUND, POLY(IMIDE-AMIDE) COPOLYMER, AND AN ARTICLE INCLUDING THE POLY(IMIDE-AMIDE) COPOLYMER

(71) Applicant: SAMSUNG ELECTRONICS CO., LTD., Suwon-si, Gyeonggi-do (KR)

(72) Inventors: Dmitry Androsov, Suwon-si (KR); Mikhail Kovalev, Suwon-si (KR); Evgeny Kiryushchenkov, Suwon-si (KR); Fedosya Kalinina, Hwaseong-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 0 days.

(21) Appl. No.: 14/341,981

(22) Filed: Jul. 28, 2014

(65) Prior Publication Data

US 2015/0148517 A1    May 28, 2015

(30) Foreign Application Priority Data

Nov. 25, 2013  (KR) .................. 10-2013-0144124

(51) Int. Cl.
| | | |
|---|---|---|
| *C08G 69/32* | (2006.01) | |
| *C07C 237/40* | (2006.01) | |
| *C08G 73/14* | (2006.01) | |
| *C08L 77/00* | (2006.01) | |
| *C08G 73/10* | (2006.01) | |
| *C08L 79/08* | (2006.01) | |

(52) U.S. Cl.
CPC ............. *C07C 237/40* (2013.01); *C08G 69/32* (2013.01); *C08G 73/10* (2013.01); *C08G 73/14* (2013.01); *C08L 77/00* (2013.01); *C08L 79/08* (2013.01)

(58) Field of Classification Search
CPC ....... C08L 79/08; C08L 77/00; C08G 69/32; C08G 73/10
See application file for complete search history.

(56) References Cited

U.S. PATENT DOCUMENTS

| | | | | |
|---|---|---|---|---|
| 5,478,914 | A | * | 12/1995 | Kaneko .............. C08G 73/1042 528/125 |
| 5,491,200 | A | | 2/1996 | Harris et al. |
| 5,494,991 | A | * | 2/1996 | Kaneko .............. C08G 73/1085 528/125 |
| 6,958,192 | B2 | | 10/2005 | Hergenrother et al. |
| 7,550,194 | B2 | | 6/2009 | Simone et al. |

FOREIGN PATENT DOCUMENTS

| | | | |
|---|---|---|---|
| JP | 2010-180349 A | | 8/2010 |
| KR | 10-2009-0070093 | * | 7/2009 |
| KR | 1020090070093 A | | 7/2009 |

OTHER PUBLICATIONS

USPTO structure search, Nov. 2015.*

* cited by examiner

*Primary Examiner* — Gregory Listvoyb
(74) *Attorney, Agent, or Firm* — Cantor Colburn LLP

(57) ABSTRACT

A compound represented by Chemical Formula 1:

Chemical Formula 1

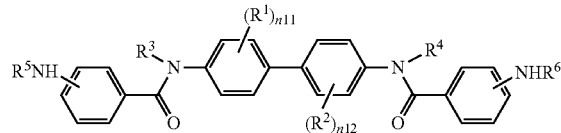

wherein in Chemical Formula 1,
$R^1$ and $R^2$ are the same or different, and are each independently an electron-withdrawing group,
$R^3$ to $R^6$ are the same or different, and are each independently selected from a hydrogen, a substituted or unsubstituted C1 to C20 alkyl group, and a substituted or unsubstituted C6 to C20 aryl group, and
n11 and n12 are the same or different, and are each independently an integer from 1 to 4.

8 Claims, 11 Drawing Sheets

COMPOUND, POLY(IMIDE-AMIDE) COPOLYMER, AND AN ARTICLE INCLUDING THE POLY(IMIDE-AMIDE) COPOLYMER

CROSS-REFERENCE TO RELATED APPLICATION

This application claims priority to Korean Patent Application No. 10-2013-0144124, filed on Nov. 25, 2013, and all the benefits accruing therefrom under 35 U.S.C. §119, the content of which is incorporated herein in its entirety by reference.

BACKGROUND

1. Field

This disclosure relates to a new compound, a poly(imide-amide) copolymer prepared using the new compound, and an article including the poly(imide-amide) copolymer.

2. Description of the Related Art

A colorless transparent material has been researched for diverse purposes such as an optical lens, a functional optical film, and a disk substrate. But as information devices are being further miniaturized and display devices providing higher resolution are developed, more functions and greater performance are desired from the material.

Therefore, there remains a need in a colorless transparent material having excellent transparency, heat resistance, mechanical strength, and flexibility to ensure high resolution.

SUMMARY

An embodiment provides a new compound used in preparing a poly(imide-amide)copolymer.

An embodiment provides a poly(imide-amide)copolymer having improved optical and thermal properties, which is prepared by using the new compound.

Another embodiment provides an article including the poly(imide-amide) copolymer.

According to an embodiment, provided is a compound represented by Chemical Formula 1:

Chemical Formula 1

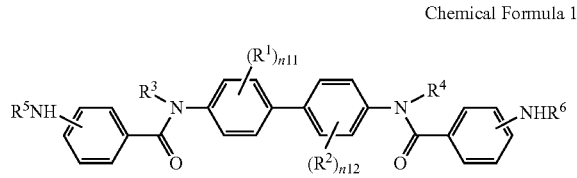

wherein in Chemical Formula 1,
$R^1$ and $R^2$ are the same or different, and are each independently an electron-withdrawing group,
$R^3$ to $R^6$ are the same or different, and are each independently selected from a hydrogen, a substituted or unsubstituted C1 to C20 alkyl group, and a substituted or unsubstituted C6 to C20 aryl group, and
n11 and n12 are the same or different, and are each independently an integer from 1 to 4.

In Chemical Formula 1, $R^1$ and $R^2$ are the same or different, and may be each independently —$CF_3$, —$CCl_3$, —$CBr_3$, —$Cl_3$, —$C_2F_5$, —$C_3F_7$, —COOH, —COOMe, —COOEt, —OMe, —OEt, —$SF_6$, —F, —Cl, or —Br.

In Chemical Formula 1, both of $R^3$ and $R^6$ may be hydrogens.

According to another embodiment, provided is a poly(imide-amide) copolymer reaction product of a diamine including a diamine represented by Chemical Formula 1 and a dianhydride represented by Chemical Formula 5:

Chemical Formula 5

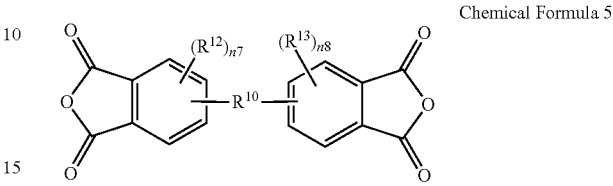

wherein in Chemical Formula 5,
$R^{10}$ is a substituted or unsubstituted C1 to C30 aliphatic group, a substituted or unsubstituted C3 to C30 alicyclic organic group, a substituted or unsubstituted C6 to C30 aromatic organic group, or a substituted or unsubstituted C2 to C30 heterocyclic group,
$R^{12}$ and $R^{13}$ are the same or different and are each independently a halogen, a hydroxyl group, a substituted or unsubstituted C1 to C10 aliphatic group, a substituted or unsubstituted C6 to C20 aromatic group, an alkoxy group of formula —$OR^{205}$, wherein $R^{205}$ is a C1 to C10 aliphatic organic group, or a silyl group of formula —$SiR^{209}R^{210}R^{211}$, wherein $R^{209}$, $R^{210}$, and $R^{211}$ are the same or different and are each independently a hydrogen or a C1 to C10 aliphatic organic group, and
n7 and n8 are the same or different and are each independently an integer ranging from 0 to 3.

In the compound represented by Chemical Formula 1, $R^1$ and $R^2$ are the same or different, and may be each independently —$CF_3$, —$CCl_3$, —$CBr_3$, —$Cl_3$, —$C_2F_5$, —$C_3F_7$, —COOH, —COOMe, —COOEt, —OMe, —OEt, —$SF_6$, —F, —Cl, or —Br.

In the compound represented by Chemical Formula 1, both of $R^3$ and $R^6$ may be the hydrogens.

The dianhydride represented by Chemical Formula 5 may be represented by at least one of Chemical Formula 6 and Chemical Formula 7:

Chemical Formula 6

Chemical Formula 7

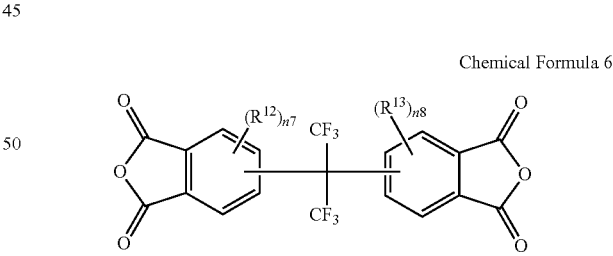

wherein in Chemical Formulae 6 and 7,
$R^{12}$ and $R^{13}$ are the same or different, and are independently a halogen, a hydroxy group, a substituted or unsubstituted C1 to C10 aliphatic organic group, a C6 to C20 aromatic organic group, an alkoxy group of formula —OR$^{208}$, wherein R$^{208}$ is a C1 to C10 aliphatic organic group, or a silyl group of formula —SiR$^{209}$R$^{210}$R$^{211}$, wherein R$^{209}$, R$^{210}$, and R$^{211}$ are the same or different, and are each independently hydrogen or a C1 to C10 aliphatic organic group, and n7 and n8 are each independently integers ranging from 0 to 3.

The diamine may further include at least one selected from a compound represented by Chemical Formula 2, a compound represented by Chemical Formula 3, and a compound represented by Chemical Formula 4:

Chemical Formula 2

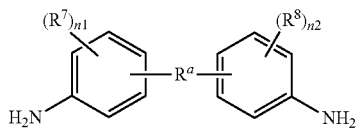

wherein in Chemical Formula 2,

R$^a$ is a substituted or unsubstituted C3 to C30 alicyclic organic group, a substituted or unsubstituted C6 to C30 aromatic organic group, or a substituted or unsubstituted C2 to C30 heterocyclic group, or a substituted or unsubstituted C13 to C20 fluorenylene group, R$^7$ and R$^8$ are the same or different and are each independently a halogen, a hydroxyl group, a substituted or unsubstituted C1 to C10 aliphatic group, a substituted or unsubstituted C6 to C20 aromatic group, an alkoxy group of formula —OR$^{200}$, wherein R$^{200}$ is a C1 to C10 aliphatic organic group, or a silyl group of formula —SiR$^{201}$R$^{202}$R$^{203}$, wherein R$^{201}$, R$^{202}$, and R$^{203}$ are the same or different and are each independently a hydrogen or a C1 to C10 aliphatic organic group, and n1 and n2 are the same or different and are each independently an integer ranging from 0 to 4:

Chemical Formula 3

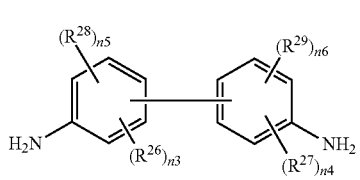

wherein in Chemical Formula 3,

R$^{26}$ and R$^{27}$ are the same or different and are each independently an electron withdrawing group, R$^{28}$ and R$^{29}$ are the same or different, and are each independently a halogen, a hydroxy group, a substituted or unsubstituted C1 to C10 aliphatic organic group, a substituted or unsubstituted C6 to C20 aromatic organic group, an alkoxy group of formula —OR$^{204}$, wherein R$^{204}$ is a C1 to C10 aliphatic organic group, or a silyl group of formula —SiR$^{205}$R$^{206}$R$^{207}$, wherein R$^{205}$, R$^{206}$, and R$^{207}$ are the same or different, and are each independently a hydrogen or a C1 to C10 aliphatic organic group, n3 is an integer ranging from 1 to 4,
n5 is an integer ranging from 0 to 3,
provided that n3+n5 is an integer ranging from 1 to 4,
n4 is an integer ranging from 1 to 4, and
n6 is an integer ranging from 0 to 3,
provided that n4+n6 is an integer ranging from 1 to 4:

Chemical Formula 4

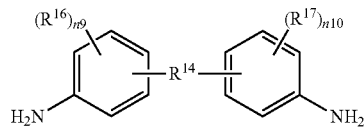

wherein in Chemical Formula 4,

R$^{14}$ is —O—, —S—, —C(=O)—, —CH(OH)—, —S(=O)$_2$—, —Si(CH$_3$)$_2$—, —(CH$_2$)$_p$—, wherein 1≤p≤10, —(CF$_2$)$_q$—, wherein 1≤q≤10, —C(CH$_3$)$_2$—, —C(CF$_3$)$_2$—, and —C(=O)NH—, or a substituted or unsubstituted C6 to C30 aromatic organic group, wherein the aromatic organic group is one aromatic ring, two or more aromatic rings fused together to provide a condensed ring system, or two or more moieties linked through a single bond or through a functional group selected from a fluorenylene group, —O—, —S—, —C(=O)—, —CH(OH)—, —S(=O)$_2$—, —Si (CH$_3$)$_2$—, —(CH$_2$)$_p$—, wherein 1≤p≤10, —(CF$_2$)$_q$—, wherein 1≤q≤10, —C(CH$_3$)$_2$—, —C(CF$_3$)$_2$—, and —C(=O)NH—, R$^{16}$ and R$^{17}$ are the same or different, and are each independently a halogen, a hydroxy group, a substituted or unsubstituted C1 to C10 aliphatic organic group, a substituted or unsubstituted C6 to C20 aromatic organic group, an alkoxy group of formula —OR$^{212}$, wherein R$^{212}$ is a C1 to C10 aliphatic organic group, or a silyl group of formula —SiR$^{213}$R$^{214}$R$^{215}$, wherein R$^{213}$, R$^{214}$, and R$^{215}$ are the same or different, and are each independently a hydrogen or a C1 to C10 aliphatic organic group, and n9 and n10 are each independently an integer ranging from 0 to 4.

In Chemical Formula 2, R$^a$ may be selected from chemical formulae:

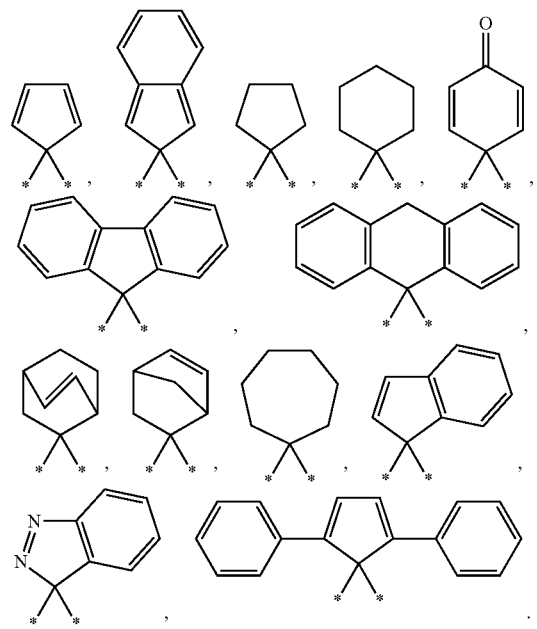

In Chemical Formula 3, $R^{26}$ and $R^{27}$ may be the same or different, and may be independently selected from —$CF_3$, —$CCl_3$, —$CBr_3$, —$Cl_3$, —$NO_2$, —CN, —C(=O)$CH_3$, and —$CO_2C_2H_5$.

In Chemical Formula 4, $R^{14}$ may be $SO_2$, and both n9 and n10 may be the integer of 0.

The poly(imide-amide) copolymer may be represented by Chemical Formula 8:

Chemical Formula 8

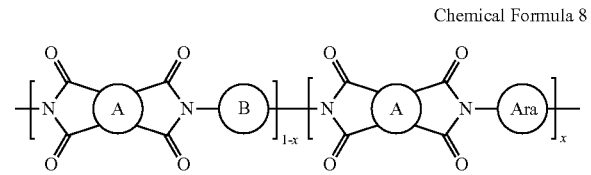

wherein in Chemical Formula 8,

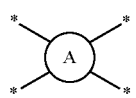

may be represented by Chemical Formula 5-1:

Chemical Formula 5-1

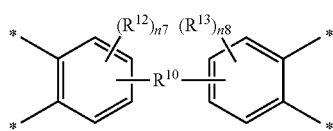

wherein in Chemical Formula 5-1, the definitions of $R^{10}$, $R^{12}$, $R^{13}$, and n7 and n8 are the same as those given in Chemical Formula 5;

wherein in Chemical Formula 8,

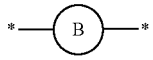

may be represented by Chemical Formula 2-1, Chemical Formula 3-1, or Chemical Formula 4-1:

Chemical Formula 2-1

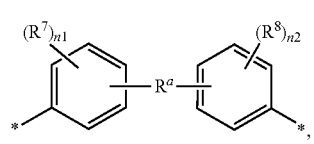

wherein in Chemical Formula 2-1, the definitions of $R^a$, $R^7$, $R^8$, and n1 and n2 are the same as those given in Chemical Formula 2;

Chemical Formula 3-1

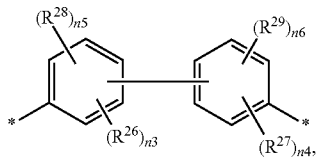

wherein in Chemical Formula 3-1, the definitions of $R^{26}$ to $R^{29}$, and n3 to n6 are the same as those given in Chemical Formula 3;

Chemical Formula 4-1

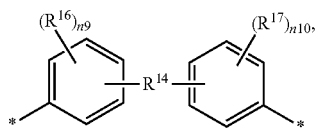

wherein in Chemical Formula 4-1, the definitions of $R^{14}$, $R^{16}$, $R^{17}$, and n9 and n10 are the same as those given in Chemical Formula 4;

wherein in Chemical Formula 8,

may be represented by Chemical Formula 9:

Chemical Formula 9

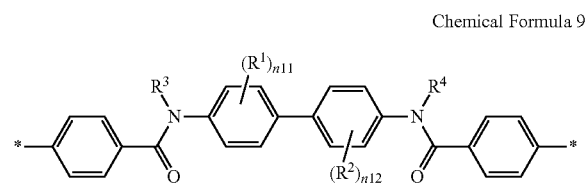

wherein in Chemical Formula 9, the definitions of $R^1$, and $R^2$, and n11 and n12 are the same as those given in Chemical Formula 1, and both $R^3$ and $R^4$ are hydrogens.

In Chemical Formula 8, x indicates the mole fraction of the unit represented by x based on 1 mole of the copolymer represented by Chemical Formula 8, i.e., 0<x<1.

For example, x may satisfy $0.01 \leq x \leq 0.10$, for example, $0.01 \leq x \leq 0.07$, and for example, $0.01 \leq x \leq 0.05$.

Chemical Formula 5-1 may be represented by Chemical Formula 6-1, or Chemical Formula 7-1:

Chemical Formula 6-1

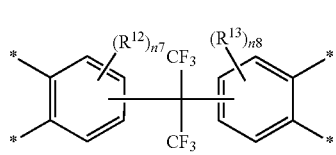

Chemical Formula 7-1

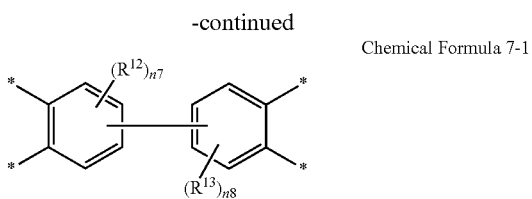

wherein in Chemical Formulae 6-1 and 7-1, the definitions of $R^{12}$, $R^{13}$, and $n_7$ and $n_8$ are the same as those given in Chemical Formula 6 and Chemical Formula 7, respectively.

According to yet another embodiment, provided is an article including the poly(imide-amide) copolymer.

In an embodiment, the article may be a film, a fiber, a coating material, or an adhesive.

The article may have a total light transmittance of greater than or equal to about 85%, in a wavelength range of 360 nanometers to 740 nanometers, the article may have light transmittance of greater than or equal to about 80% in a wavelength of 430 nanometers, and the article may have light transmittance of greater than or equal to about 50% in a wavelength of 400 nanometers.

The article may have a yellowness index ("YI") of less than or equal to about 5.

The article may have a birefringence of less than or equal to about 0.10.

The article may have a coefficient of thermal expansion ("CTE") of less than or equal to about 10 parts per million per degree Centigrade ("ppm/° C."), for example, of less than or equal to about 7.5 ppm/° C., in a temperature range of 50° C. to 150° C.

The article may have a coefficient of thermal expansion ("CTE") of less than or equal to about 15 parts per million per degree Centigrade ("ppm/° C."), for example, of less than or equal to about 12.5 ppm/° C., in a temperature range of 50° C. to 250° C.

The article may have a coefficient of thermal expansion ("CTE") of less than or equal to about 20 parts per million per degree Centigrade ("ppm/° C."), for example, of less than or equal to about 18 ppm/° C., in a temperature range of 50° C. to 300° C.

The article may have a glass transition temperature ("Tg") of greater than or equal to about 300° C., for example, of greater than or equal to about 330° C.

The article may have a 1.0% weight degradation temperature ("Td(1.0%)") of greater than or equal to about 500° C.

The article may have a 5.0% weight degradation temperature ("Td(5.0%)") of greater than or equal to about 550° C.

According to still another embodiment, provided is a display device including the article.

The display device may be a liquid crystal device ("LCD"), an organic light emitting diode ("OLED") or a complementary metal-oxide semiconductor ("CMOS").

Hereinafter, further embodiments will be described in detail.

BRIEF DESCRIPTION OF THE DRAWINGS

The above and other aspects, advantages and features of this disclosure will become more apparent by describing in further detail exemplary embodiments thereof with reference to the accompanying drawings, in which:

FIG. 1B is enlarged view of a part of FIG. 1A;

FIG. 2B is enlarged view of a part of FIG. 2A;

DETAILED DESCRIPTION

Figure 1A:
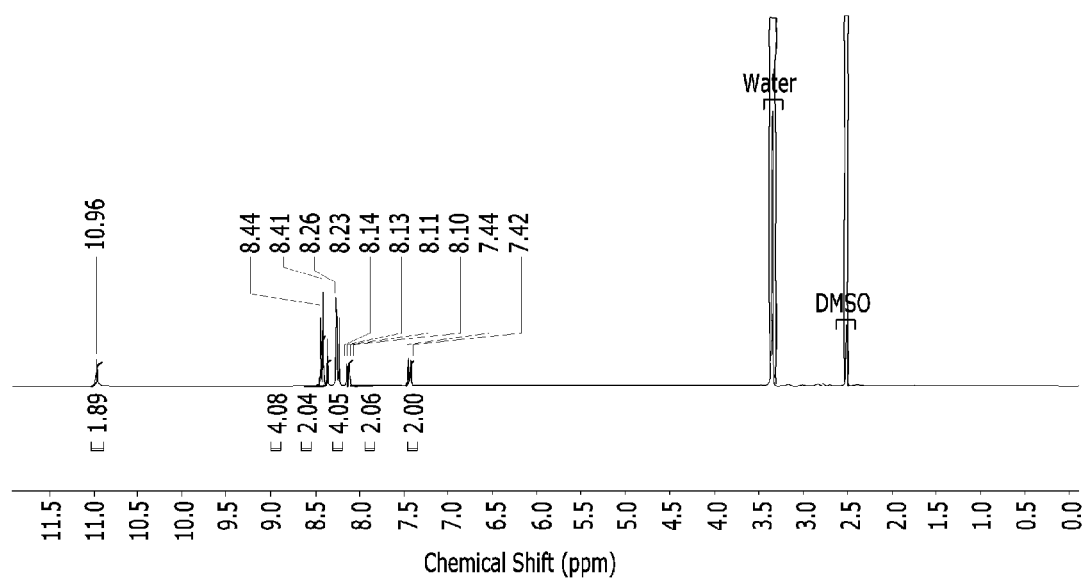
FIGS. 1A and 1B are graphs of peak intensity versus chemical shift (parts per million, ppm) illustrating $^1$H NMR spectra of DA167, a precursor of a new diamine DA168 according to an embodiment.

This disclosure will be described more fully hereinafter with reference to the accompanying drawings, in which embodiments are shown. This disclosure may, however, be embodied in many different forms and is not to be construed as limited to the exemplary embodiments set forth herein.

It will be understood that when an element is referred to as being "on" another element, it may be directly on the other element or intervening elements may be present therebetween. In contrast, when an element is referred to as being "directly on" another element, there are no intervening elements present.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, a first element, component, region, layer, or section discussed below could be termed a second element, component, region, layer, or section without departing from the teachings of the present embodiments.

The terminology used herein is for the purpose of describing present embodiments only and is not intended to be limiting. As used herein, the singular forms "a," "an" and "the" are intended to include the plural forms as well, unless the context clearly indicates otherwise. The term "or" means "and/or." As used herein, the term "and/or" includes any and all combinations of one or more of the associated listed items. Expressions such as "at least one of," when preceding a list of elements, modify the entire list of elements and do not modify the individual elements of the list.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"Mixture" as used herein is inclusive of all types of combinations, including blends, alloys, solutions, and the like.

As used herein, when a specific definition is not otherwise provided, the term "substituted" refers to a group or compound substituted with at least one substituent including a halogen (—F, —Br, —Cl, or —I), a hydroxyl group, a nitro group, a cyano group, an amino group (—NH$_2$, —NH(R$^{100}$) or —N(R$^{101}$)(R$^{102}$), wherein R$^{100}$, R$^{101}$, and R$^{102}$ are the same or different, and are each independently a C1 to C10 alkyl group, an amidino group, a hydrazine group, a hydrazone group, a carboxyl group, an ester group, a ketone group, a substituted or unsubstituted alkyl group, a substituted or unsubstituted alicyclic organic group, a substituted or unsubstituted aryl group, a substituted or unsubstituted alkenyl group, a substituted or unsubstituted alkynyl group, a substituted or unsubstituted heteroaryl group, and a substituted or unsubstituted heterocyclic group, in place of at least one hydrogen of a functional group, or the substituents may be linked to each other to provide a ring.

As used herein, the term "alkyl group" refers to a straight or branched chain saturated aliphatic hydrocarbon having the specified number of carbon atoms and having a valence of at least one. Non-limiting examples of the alkyl group are methyl, ethyl, and propyl.

As used herein, the term "alkoxy group" refers to "alkyl-O—", wherein the term "alkyl" has the same meaning as described above. Non-limiting examples of the alkoxy group are methoxy, ethoxy, propoxy, cyclopropoxy, and cyclohexyloxy.

As used herein, the term "aryl group", which is used alone or in combination, refers to an aromatic hydrocarbon containing at least one ring. Non-limiting examples of the aryl group are phenyl, naphthyl, and tetrahydronaphthyl.

As used herein, when a specific definition is not otherwise provided, the term "alkyl group" refers to a C1 to C30 alkyl group, for example a C1 to C15 alkyl group such as methyl ("Me") or ethyl ("Et"), the term "cycloalkyl group" refers to a C3 to C30 cycloalkyl group, for example a C3 to C18 cycloalkyl group, the term "alkoxy group" refer to a C1 to C30 alkoxy group, for example a C1 to C18 alkoxy group, the term "ester group" refers to a C2 to C30 ester group, for example a C2 to C18 ester group, the term "ketone group" refers to a C2 to C30 ketone group, for example a C2 to C18 ketone group, the term "aryl group" refers to a C6 to C30 aryl group, for example a C6 to C18 aryl group, the term "alkenyl group" refers to a C2 to C30 alkenyl group, for example a C2 to C18 alkenyl group, the term "alkynyl group" refers to a C2 to C30 alkynyl group, for example a C2 to C18 alkynyl group, the term "alkylene group" refers to a C1 to C30 alkylene group, for example a C1 to C18 alkylene group, and the term "arylene group" refers to a C6 to C30 arylene group, for example a C6 to C16 arylene group.

As used herein, when a specific definition is not otherwise provided, the term "aliphatic" refers to a C1 to C30 alkyl group, a C2 to C30 alkenyl group, a C2 to C30 alkynyl group, a C1 to C30 alkylene group, a C2 to C30 alkenylene group, or a C2 to C30 alkynylene group, for example a C1 to C15 alkyl group, a C2 to C15 alkenyl group, a C2 to C15 alkynyl group, a C1 to C15 alkylene group, a C2 to C15 alkenylene group, or a C2 to C15 alkynylene group, the term "alicyclic organic group" refers to a C3 to C30 cycloalkyl group, a C3 to C30 cycloalkenyl group, a C3 to C30 cycloalkynyl group, a C3 to C30 cycloalkylene group, a C3 to C30 cycloalkenylene group, or a C3 to C30 cycloalkynylene group, for example a C3 to C15 cycloalkyl group, a C3 to C15 cycloalkenyl group, a C3 to C15 cycloalkynyl group, a C3 to C15 cycloalkylene group, a C3 to C15 cycloalkenylene group, or a C3 to C15 cycloalkynylene group.

As used herein when a definition is not otherwise provided, the term "aromatic organic group" refers to a C6 to C30 group comprising one aromatic ring, two or more aromatic rings fused together to provide a condensed ring system, or two or more moieties independently selected from the foregoing (a single aromatic ring or a condensed ring system) linked through a single bond or through a functional group selected from a fluorenylene group, —O—, —S—, —C(=O)—, —CH(OH)—, —S(=O)$_2$—, —Si(CH$_3$)$_2$—, —(CH$_2$)$_p$—, wherein 1≤p≤10, —(CF$_2$)$_q$—, wherein 1≤q≤10, —C(CH$_3$)$_2$—, —C(CF$_3$)$_2$—, and —C(=O)NH—, for example through —S(=O)$_2$—, for example an aryl group or a C6 to C30 arylene group, for example a C6 to C16 aryl group or a C6 to C16 arylene group such as phenylene. An example of an aromatic organic group is a fluorenylene group.

As used herein, when a specific definition is not otherwise provided, the term "heterocyclic group" refers to a C2 to C30 cycloalkyl group, a C2 to C30 cycloalkylene group, a C2 to C30 cycloalkenyl group, a C2 to C30 cycloalkenylene group, a C2 to C30 cycloalkynyl group, a C2 to C30 cycloalkynylene group, a C2 to C30 heteroaryl group, or a C2 to C30 heteroarylene group including 1 to 3 heteroatoms selected from O, S, N, P, Si, and a combination thereof in one ring, for example a C2 to C15 cycloalkyl group, a C2 to C15 cycloalkylene group, a C2 to C15 cycloalkenyl group, a C2 to C15 cycloalkenylene group, a C2 to C15 cycloalkynyl group, a C2 to C15 cycloalkynylene group, a C2 to C15 heteroaryl group, or a C2 to C15 heteroarylene group including 1 to 3 heteroatoms selected from O, S, N, P, Si, and a combination thereof, in one ring.

As used herein, when a definition is not otherwise provided, "combination" commonly refers to mixing or copolymerization.

As used herein, when a definition is not otherwise provide, "electron-withdrawing group" refers to an atom or group that withdraws electron density from a conjugated π system via an inductive or resonance electron effect, thus making the π system more electrophilic.

In addition, in the specification, the mark "*" may refer to a point of attachment to another atom.

According to an embodiment, provided is a new diamine monomer including an aramid structure therein. The diamine may be represented by Chemical Formula 1:

Chemical Formula 1

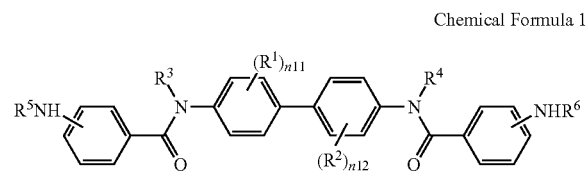

In Chemical Formula 1, $R^1$ and $R^2$ are the same or different, and are each independently an electron-withdrawing group, $R^3$ to $R^6$ are the same or different, and are each independently selected from a hydrogen, a substituted or unsubstituted C1 to C20 alkyl group, and a substituted or unsubstituted C6 to C20 aryl group, n11 and n12 are the same or different, and are each independently an integer from 1 to 4.

In Chemical Formula 1, $R^1$ and $R^2$ are the same or different, and may be each independently —$CF_3$, —$CCl_3$, —$CBr_3$, —$Cl_3$, —$C_2F_5$, —$C_3F_7$, —COOH, —COOMe, —COOEt, —OMe, —OEt, —$SF_6$, —F, —Cl, or —Br.

In Chemical Formula 1, $R^3$ to $R^6$ may be the same or different, and may be each independently hydrogen, or C1 to C4 alkyl group.

In an exemplary embodiment, both $R^1$ and $R^2$ may be —$CF_3$, and all of $R^3$ to $R^6$ may be hydrogens.

The compound represented by Chemical Formula 1 includes amide groups therein, as well as amino groups at both ends thereof, and thus, may be used to directly prepare a poly(imide-aramid) copolymer by a reaction of the compound and a dianhydride without involving a reaction of a dicarboxylic acid derivative and a diamine to provide an aramide.

Also, a poly(imide-amide) film prepared by reacting the compound represented by Chemical Formula 1 as a diamine monomer with a dianhydride has a drastically decreased coefficient of thermal expansion ("CTE"), while maintaining excellent optical and thermal properties compared to the conventional poly(imide-amide) films prepared without using the compound.

Polyimide has excellent thermal, chemical, mechanical, and optical properties, and thus is used in various elements of electric devices. Especially for the electronics industry, improvements of polyimides are desired to form tough, pin-hole free coatings, having a low dielectric constant, low moisture absorption, a low linear coefficient of thermal expansion, and good mechanical properties. It is not usually possible to maximize all properties, since many of them are antagonistic. Thus, only a compromised solution is usually achieved by at least partially sacrificing one or more of these properties in order to maximize a desired one.

Especially important properties for electronics, and other applications as well, is low linear thermal expansion coefficient ("CTE"), high glass transition temperature ("Tg"), and good optical transparency. Achieving a low CTE is especially important, as in electronic components, differences in the expansion coefficients of the components that make up the electronic device can generate stresses in the device which may lead to premature device failure. As electronic components become ever smaller, control of stress becomes an even greater concern. Accordingly, the thermal expansions of the various components of a device should be matched as closely as possible.

Figure 7:
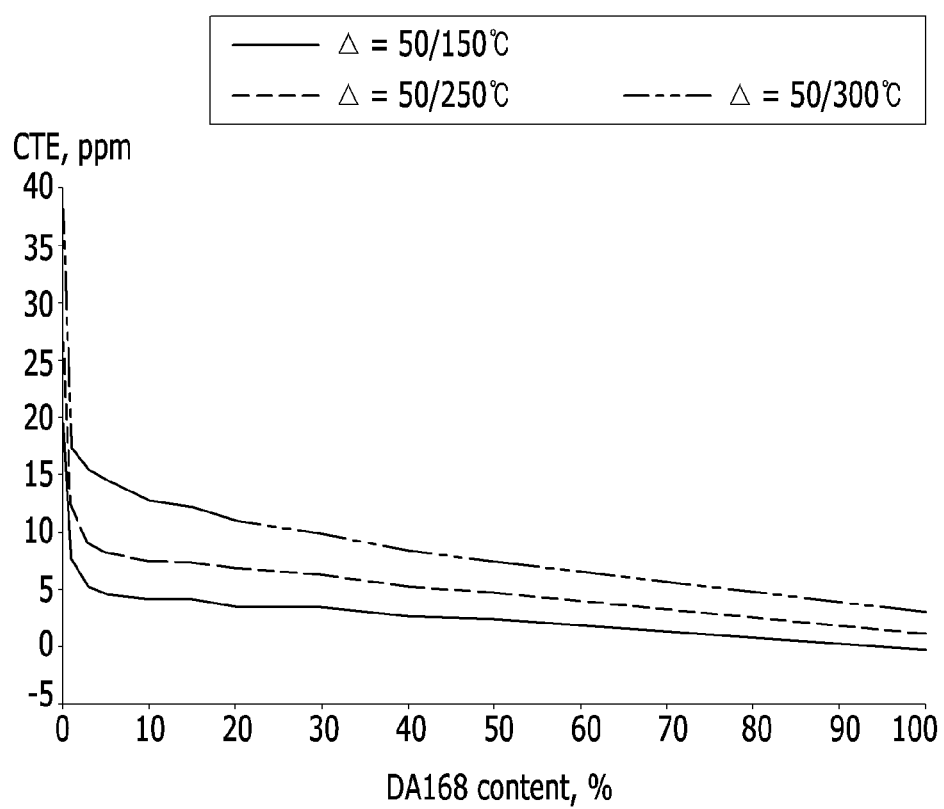
FIG. 7 shows graphs of coefficient of thermal expansion ("CTE") (parts per million per degree Centigrade, ppm/° C.) versus DA168 content (percent, %) at different temperature ranges, showing changes of CTE of poly(imide-amide) films.
Figure 8:
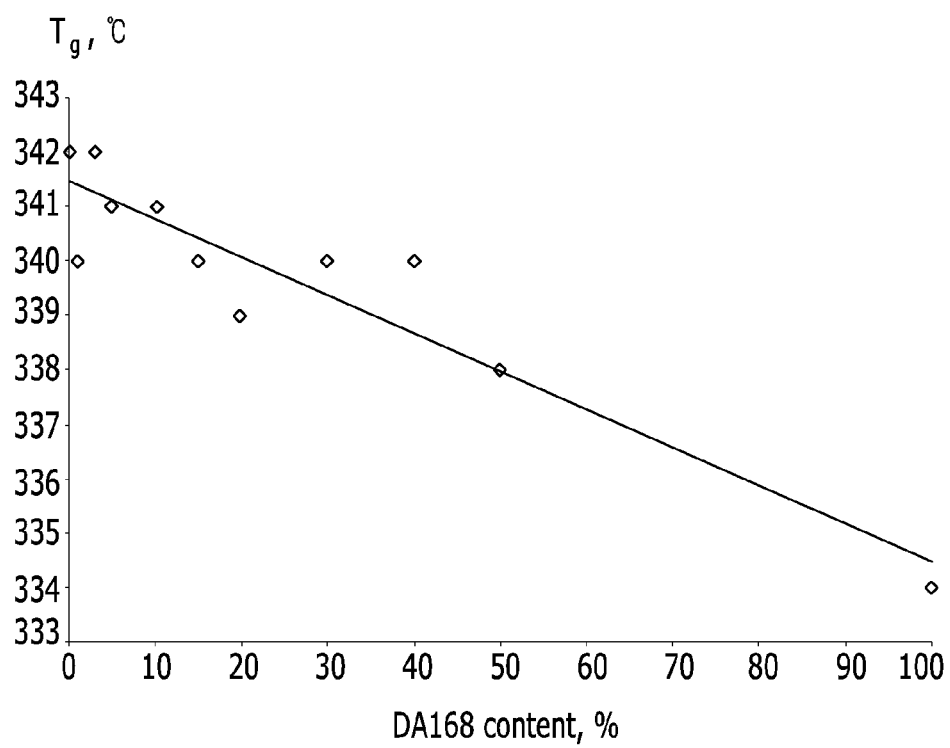
FIG. 8 is a graph of glass transition temperature ("Tg") of poly(imide-amide) films versus DA168 content (percent, %)
Figure 9:
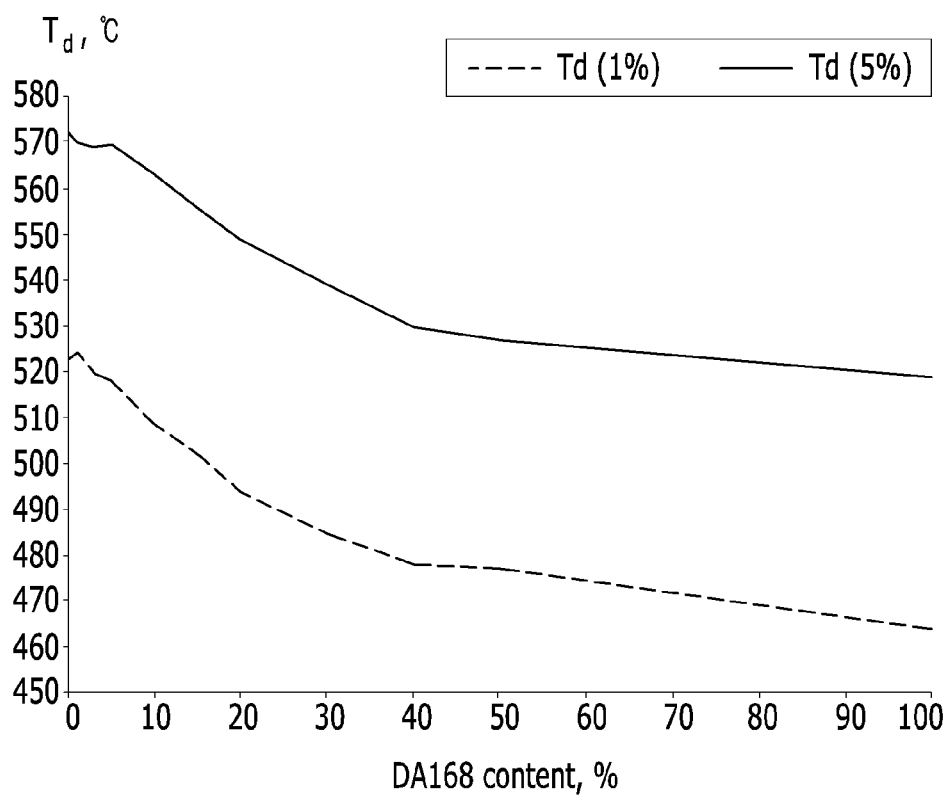
FIG. 9 shows graphs of 1% weight degradation temperature and 5% weight degradation temperature of poly(imide-amide) films (° C., degrees Centigrade) versus DA168 content (percent, %).

As shown in FIG. 7, poly(imide-amide) films prepared by using the compound represented by Chemical Formula 1 as a diamine monomer have a decreased CTE in all temperature ranges, compared to the poly(imide-amide) films that do not include the compound. Especially, the poly(imide-amide) films prepared by using the compound represented by Chemical Formula 1 at a specific content have a drastically decreased CTE, while maintaining excellent optical and thermal properties compared to the conventional poly(imide-amide) films prepared without using the compound.

As described in detail in the Examples, the poly(imide-amide) films prepared by reacting the new diamine compound represented by Chemical Formula 1 with a dianhidride, such as, for example, 3,3',4,4'-biphenyltetracarboxylic dianhydride ("BPDA"), as well as a conventional diamine monomer, for example, 2,2'-bis(trifluoromethyl)benzidine ("TFDB"), at specific ratios, for example, by using the compound represented by Chemical Formula 1 of less than or equal to about 10 mol % based on the total mole number of the diamines used, the poly(imide-amide) films have a dramatically lowered CTE compared to a poly(imide-amide) film prepared by using only TFDB and BPDA as monomers, as well as maintain excellent optical and thermal properties of the poly(imide-amide) film prepared by using only TFDB and BPDA as monomers. The effects of the compound represented by Chemical Formula 1 as above are confirmed by the instant Examples and Drawings.

The compound represented by Chemical Formula 1 may be prepared by mixing and reacting biphenyl diamine substituted with two electron withdrawing groups, $R^1$ and $R^2$, and an acyl halide, such as, for example, para-nitro benzoyl chloride, at a mole ratio of 1:2, as below.

Reaction Scheme 1

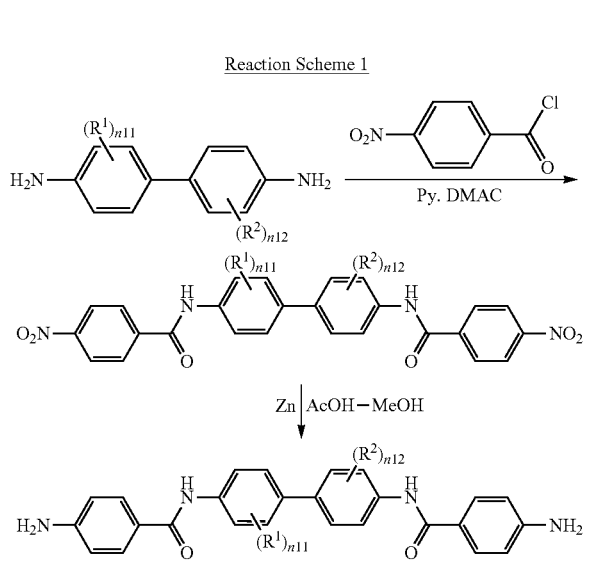

As shown from the above Reaction Formula 1, a precursor compound having nitro groups at both ends thereof is first prepared by reacting a biphenyl diamine substituted with two electron withdrawing groups and para-nitro benzoyl chlorides, following by a reduction of the precursor compound to the final product represented by Chemical Formula 1. Although both end groups of the compound are described as amino groups in the above Reaction Formula 1, it is well known to persons skilled in the art that one or more hydrogens attached to the amino group may be substituted with an alkyl or another functional group. By substituting hydrogens of the amino groups at both ends thereof with other functional groups, various compounds represented by Chemical Formula 1 may be prepared.

Figure 2A:
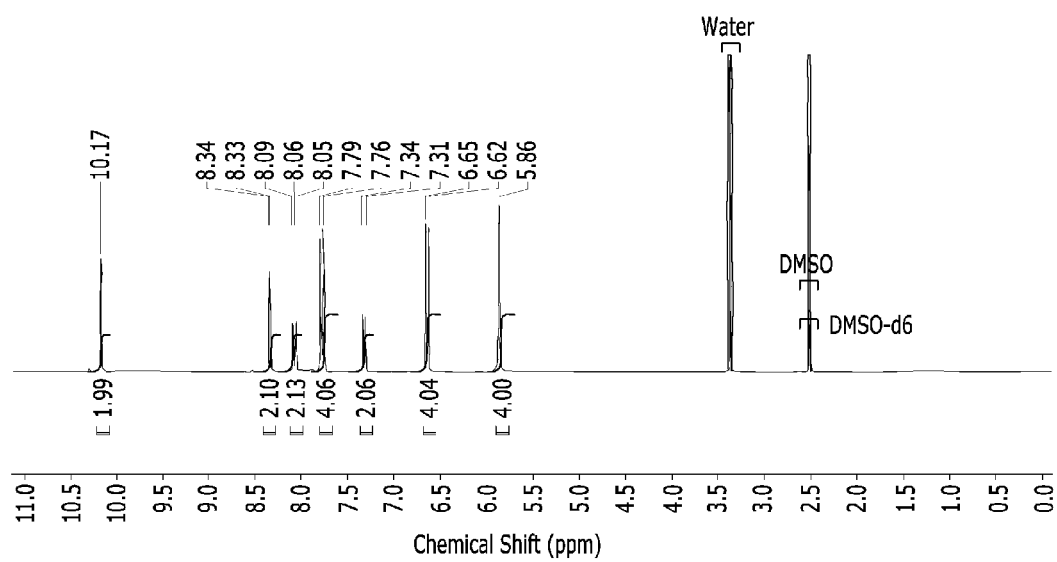
FIGS. 2A and 2B are graphs of peak intensity versus chemical shift (parts per million, ppm) illustrating $^1$H NMR spectra of DA168, a new diamine according to an embodiment.
Figure 2B:
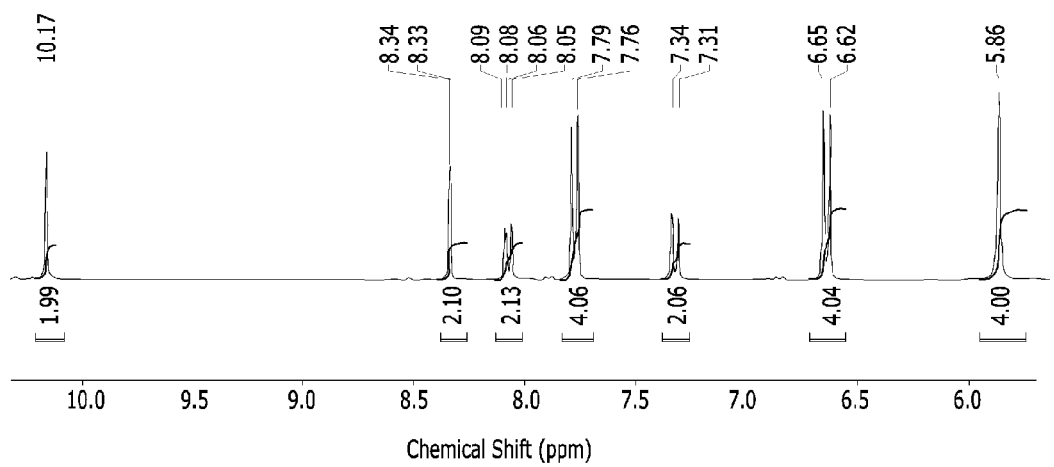

FIGS. 2A and 2B are graphs of peak intensity versus chemical shift (parts per million, ppm) illustrating $^1$H NMR spectra of DA168, a new diamine according to an embodiment. DA168 is a compound prepared as an example, in which both ends thereof have amino groups, and both $R^1$ and $R^2$ in Chemical Formula 1 are —$CF_3$ groups.

Figure 1B:
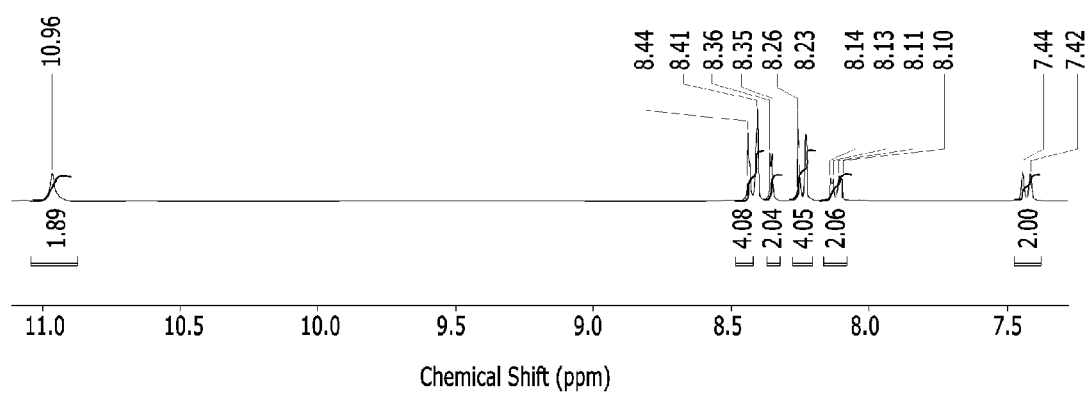

FIGS. 1A and 1B are graphs of peak intensity versus chemical shift (parts per million, ppm) illustrating $^1$H NMR spectra of DA167, a precursor of DA168, which has nitro groups at both ends thereof before being reduced to amino groups.

Figure 3:
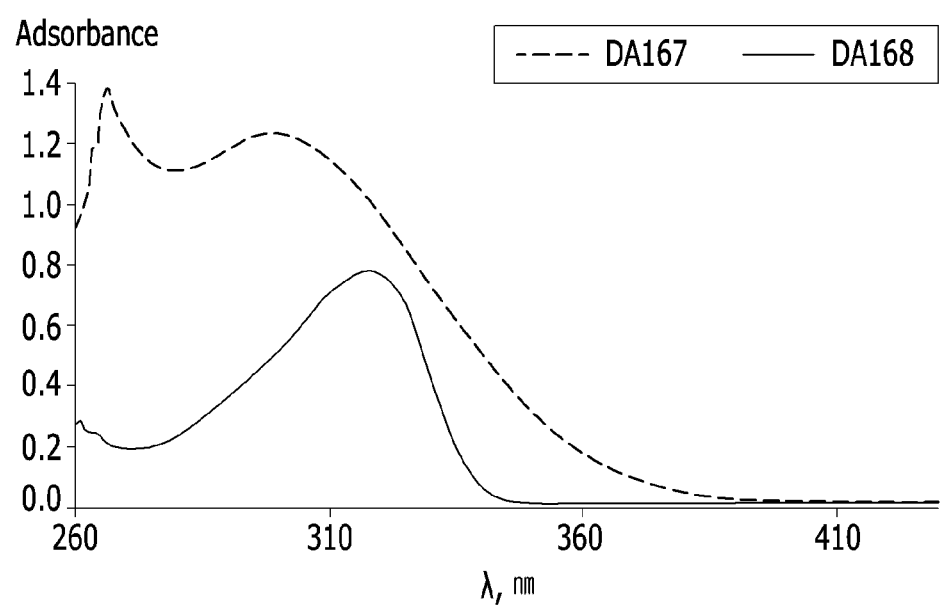
FIG. 3 is a graph of adsorbance ("λ") (arbitrary units, a.u.) versus wavelength (nanometers, nm) showing ultra violet absorption of DA168, a new diamine, and DA167, a precursor of the new diamine, respectively.
Figure 4:
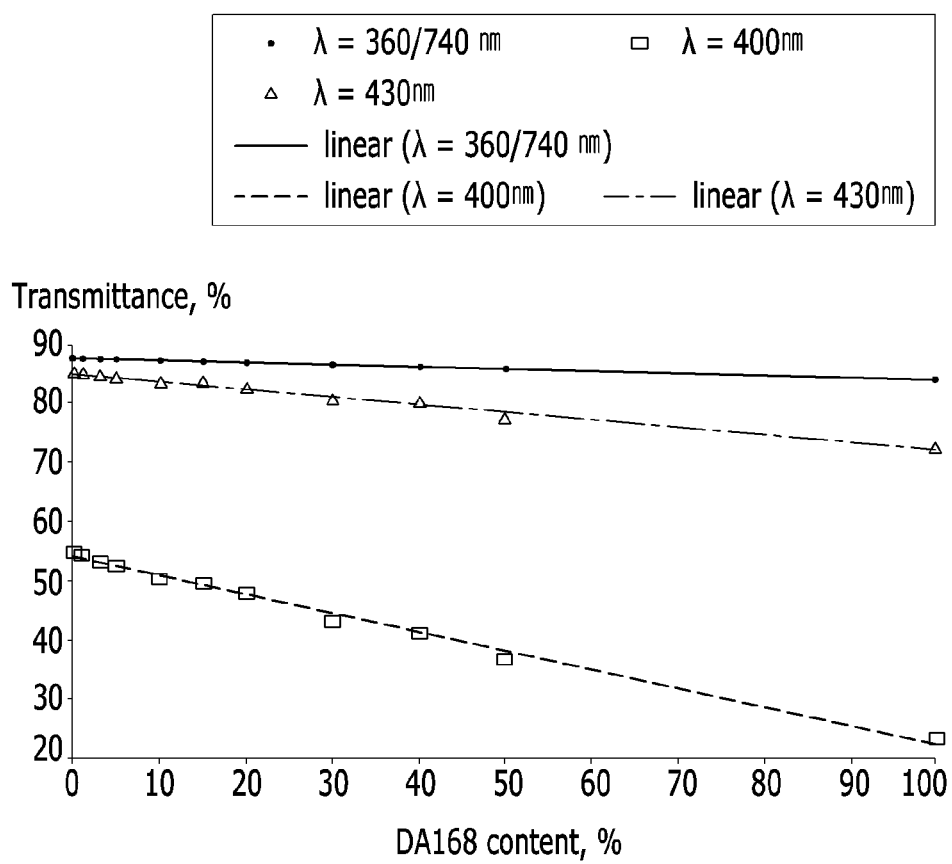
FIG. 4 is a graph of transmittance (percent, %) versus DA168 content (percent, %) showing of transmittance at different wavelengths of poly(imide-amide) films versus DA168 content (%)
Figure 5:
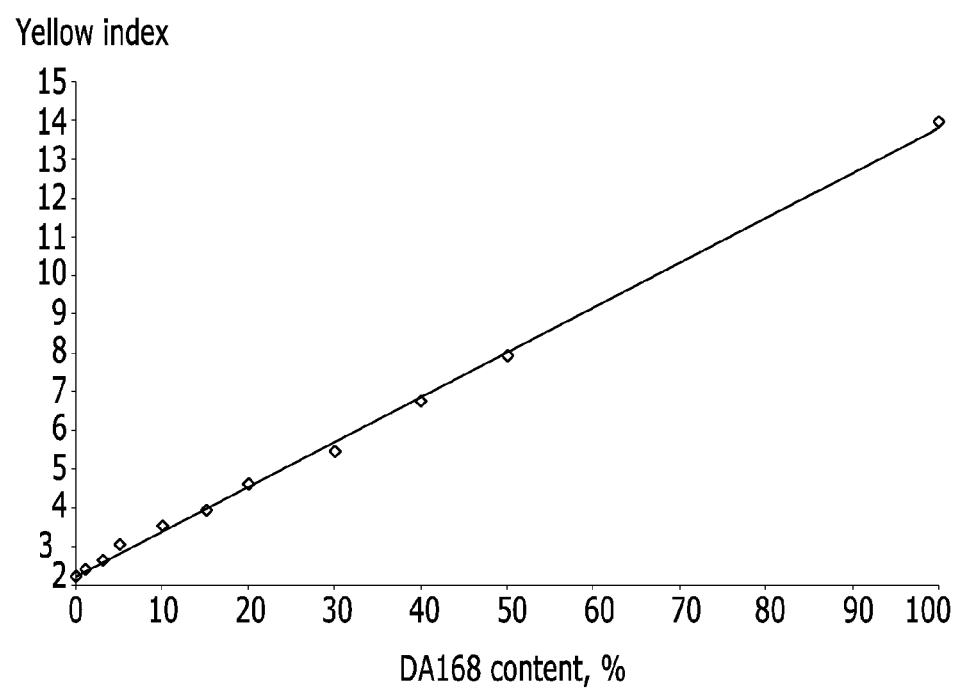
FIG. 5 is a graph of yellowness index ("YI") of poly(imide-amide) films versus DA168 content (percent, %)
Figure 6:
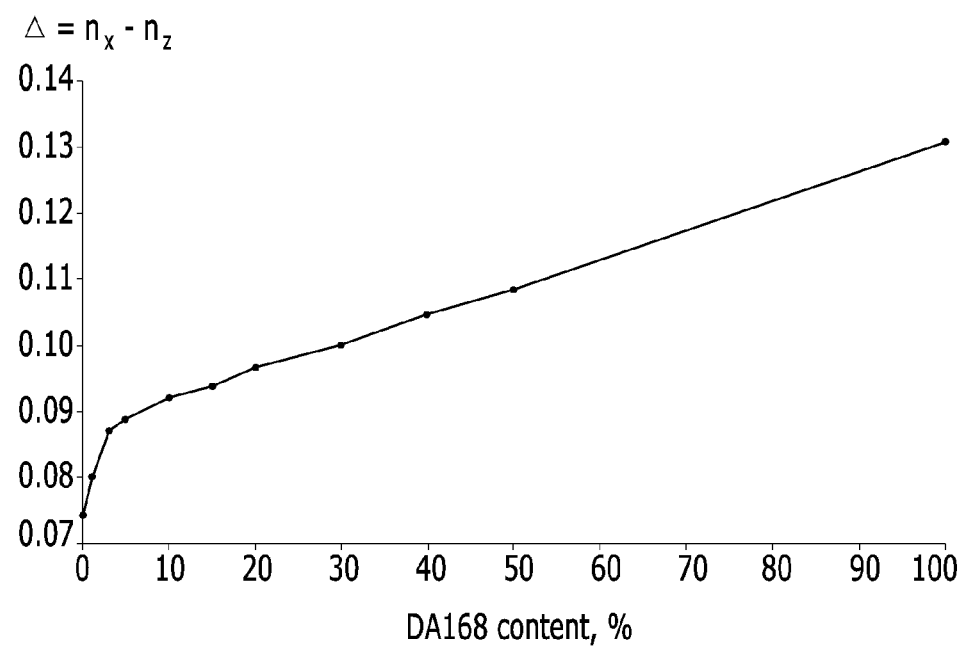
FIG. 6 is a graph of birefringence ("Δ") of poly(imide-amide) films versus DA168 content (percent, %)

FIG. 3 shows graphs of ultra violet absorption of DA167 and DA168.

Through FIG. 1 to FIG. 3, it is confirmed that DA168 is prepared by reducing DA167.

According to another embodiment, provided is a poly (imide-amide) copolymer reaction product of a diamine including a diamine represented by the above Chemical Formula 1 and a dianhydride represented by Chemical Formula 5.

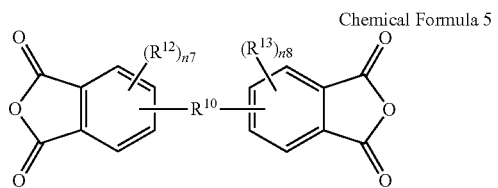

Chemical Formula 5

In Chemical Formula 5, $R^{10}$ is a substituted or unsubstituted C1 to C30 aliphatic group, a substituted or unsubstituted C3 to C30 alicyclic organic group, a substituted or unsubstituted C6 to C30 aromatic organic group, or a substituted or unsubstituted C2 to C30 heterocyclic group, $R^{12}$ and $R^{13}$ are the same or different and are each independently a halogen, a hydroxyl group, a substituted or unsubstituted C1 to C10 aliphatic group, a substituted or unsubstituted C6 to C20 aromatic group, an alkoxy group of formula —$OR^{205}$, wherein $R^{205}$ is a C1 to C10 aliphatic organic group, or a silyl group of formula —$SiR^{209}R^{210}R^{211}$, wherein $R^{209}$, $R^{210}$, and $R^{211}$ are the same or different and are each independently a hydrogen, or a C1 to C10 aliphatic organic group, and n7 and n8 are the same or different and are each independently an integer ranging from 0 to 3.

The dianhydride represented by above Chemical Formula 5 may be represented by at least one of Chemical Formula 6 and Chemical Formula 7:

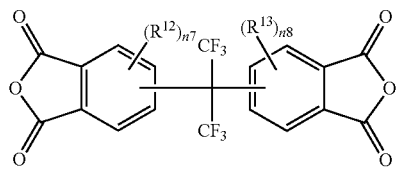

Chemical Formula 6

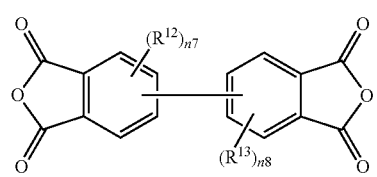

Chemical Formula 7

In Chemical Formulae 6 and 7, $R^{12}$ and $R^{13}$ are the same or different, and are each independently a halogen, a hydroxy group, a substituted or unsubstituted C1 to C10 aliphatic organic group, a C6 to C20 aromatic organic group, an alkoxy group of formula —$OR^{208}$, wherein $R^{208}$ is a C1 to C10 aliphatic organic group, or a silyl group of formula —$SiR^{209}R^{210}R^{211}$, wherein $R^{209}$, $R^{210}$, and $R^{211}$ are the same or different, and are each independently hydrogen or a C1 to C10 aliphatic organic group, and n7 and n8 are each independently integers ranging from 0 to 3.

In an example, in Chemical Formula 1, both $R^1$ and $R^2$ may be —$CF_3$ groups, each substituted at ortho position of each phenyl group, and all of $R^3$ to $R^6$ may be hydrogens.

The diamine may further include another diamine, in addition to the diamine represented by Chemical Formula 1.

The additional diamine may be at least one selected from Chemical Formula 2, Chemical Formula 3, and Chemical Formula 4:

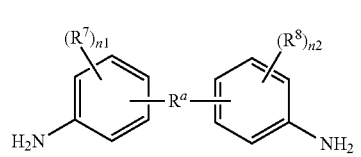

Chemical Formula 2

In Chemical Formula 2, $R^a$ is a substituted or unsubstituted C3 to C30 alicyclic organic group, a substituted or unsubstituted C6 to C30 aromatic organic group, or a substituted or unsubstituted C2 to C30 heterocyclic group, or a substituted or unsubstituted C13 to C20 fluorenylene group, $R^7$ and $R^8$ are the same or different and are each independently a halogen, a hydroxyl group, a substituted or unsubstituted C1 to C10 aliphatic group, a substituted or unsubstituted C6 to C20 aromatic group, an alkoxy group of formula —$OR^{200}$, wherein $R^{200}$ is a C1 to C10 aliphatic organic group, or a silyl group of formula —$SiR^{201}R^{202}R^{203}$, wherein $R^{201}$, $R^{202}$, and $R^{203}$ are the same or different and are each independently a hydrogen or a C1 to C10 aliphatic organic group, and n1 and n2 are the same or different and are each independently an integer ranging from 0 to 4.

Chemical Formula 3

[Chemical structure of Formula 3: biphenyl diamine with substituents (R²⁸)ₙ₅, (R²⁹)ₙ₆, (R²⁶)ₙ₃, (R²⁷)ₙ₄ and two NH₂ groups]

In Chemical Formula 3, $R^{26}$ and $R^{27}$ are the same or different and are each independently an electron withdrawing group, $R^{28}$ and $R^{29}$ are the same or different, and are each independently a halogen, a hydroxy group, a substituted or unsubstituted C1 to C10 aliphatic organic group, a substituted or unsubstituted C6 to C20 aromatic organic group, an alkoxy group of formula —$OR^{204}$, wherein $R^{204}$ is a C1 to C10 aliphatic organic group, or a silyl group of formula —$SiR^{205}R^{206}R^{207}$, wherein $R^{205}$, $R^{206}$, and $R^{207}$ are the same or different, and are each independently a hydrogen or a C1 to C10 aliphatic organic group, n3 is an integer ranging from 1 to 4, n5 is an integer ranging from 0 to 3, provided that n3+n5 is an integer ranging from 1 to 4, n4 is an integer ranging from 1 to 4, and n6 is an integer ranging from 0 to 3, provided that n4+n6 is an integer ranging from 1 to 4.

Chemical Formula 4

[Chemical structure of Formula 4: diamine with R¹⁴ linker and substituents (R¹⁶)ₙ₉, (R¹⁷)ₙ₁₀]

In Chemical Formula 4, $R^{14}$ is —O—, —S—, —C(=O)—, —CH(OH)—, —S(=O)₂—, —Si(CH₃)₂—, —(CH₂)ₚ—, wherein 1≤p≤10, —(CF₂)_q—, wherein 1≤q≤10, —C(CH₃)₂—, —C(CF₃)₂—, and —C(=O)NH—, or a substituted or unsubstituted C6 to C30 aromatic organic group, wherein the aromatic organic group includes one aromatic ring, two or more aromatic rings fused together to provide a condensed ring system, or two or more moieties linked through a single bond or through a functional group selected from a fluorenylene group, —O—, —S—, —C(=O)—, —CH(OH)—, —S(=O)₂—, —Si(CH₃)₂—, —(CH₂)ₚ—, wherein 1≤p≤10, —(CF₂)_q—, wherein 1≤q≤10, —C(CH₃)₂—, —C(CF₃)₂—, and —C(=O)NH—, $R^{16}$ and $R^{17}$ are the same or different, and are each independently a halogen, a hydroxy group, a substituted or unsubstituted C1 to C10 aliphatic organic group, a substituted or unsubstituted C6 to C20 aromatic organic group, an alkoxy group of formula —$OR^{212}$, wherein $R^{212}$ is a C1 to C10 aliphatic organic group, or a silyl group of formula —$SiR^{213}R^{214}R^{215}$, wherein $R^{213}$, $R^{214}$, and $R^{215}$ are the same or different, and are each independently a hydrogen or a C1 to C10 aliphatic organic group, and n9 and n10 are each independently an integer ranging from 0 to 4.

In Chemical Formula 2, $R^a$ may be selected from the following chemical formulae:

[Various cyclic and aromatic chemical structures shown]

In Chemical Formula 3, $R^{26}$ and $R^{27}$ may be the same or different, and may be each independently selected from —CF₃, —CCl₃, —CBr₃, —Cl₃, —NO₂, —CN, —C(=O)CH₃, and —CO₂C₂H₅.

In Chemical Formula 4, $R^{14}$ may be SO₂, and both n9 and n10 may be the integer of 0.

The poly(imide-amide) copolymer may be represented by Chemical Formula 8:

Chemical Formula 8

[Chemical structure of Formula 8: copolymer structure with repeating units containing A, B, and Ara groups]

In Chemical Formula 8,

[Chemical structure showing A group]

may be represented by Chemical Formula 5-1.

Chemical Formula 5-1

[Chemical structure of Formula 5-1: biphenyl structure with R¹⁰ linker and substituents (R¹²)ₙ₇, (R¹³)ₙ₈]

In Chemical Formula 5-1, the definitions of $R^{10}$, $R^{12}$, $R^{13}$, and n7 and n8 are the same as those given in Chemical Formula 5.

The Chemical Formula 5-1 may be represented by Chemical Formula 6-1 or Chemical Formula 7-1.

Chemical Formula 6-1

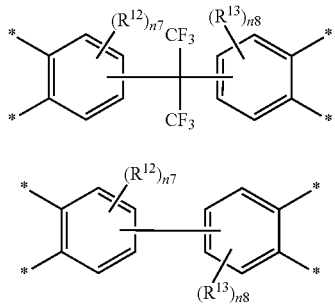

Chemical Formula 7-1

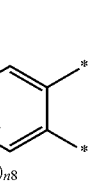

In Chemical Formulae 6-1 and 7-1, the definitions of $R^{12}$, and $R^{13}$, and n7 and n8 are the same as those given in Chemical Formulae 6 and 7.

In Chemical Formula 8,

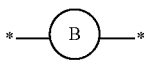

may be derived from a diamine, and may be represented by following Chemical Formula 2-1, Chemical Formula 3-1, or Chemical Formula 4-1.

Chemical Formula 2-1

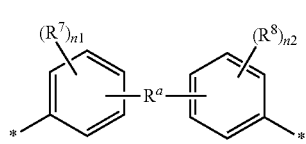

In Chemical Formula 2-1, the definitions of $R^a$, $R^7$, $R^8$, and n1 and n2 are the same as those given in Chemical Formula 2.

Chemical Formula 3-1

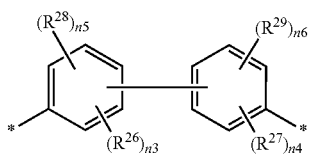

In Chemical Formula 3-1, the definitions of $R^{26}$ to $R^{29}$, and n3 to n6 are the same as those given in Chemical Formula 3.

Chemical Formula 4-1

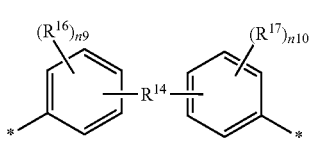

In Chemical Formula 4-1, the definitions of $R^{14}$, $R^{16}$, $R^{17}$, and n9 and n10 are the same as those given in Chemical Formula 4.

In Chemical Formula 8,

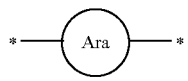

may be derived from the compound represented by Chemical Formula 1, by deleting the amino groups from both ends thereof, and may be represented by Chemical Formula 9.

Chemical Formula 9

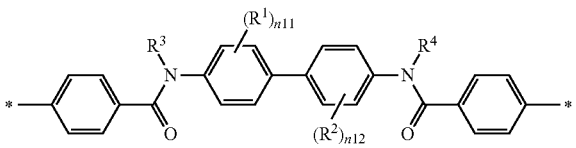

In Chemical Formula 9, the definitions of $R^1$, and $R^2$, and n11 and n12 are the same as those given in Chemical Formula 1, and both $R^3$ and $R^4$ are hydrogens.

In Chemical Formula 8, x indicates the mole fraction of the unit represented by x based on 1 mole of the copolymer represented by Chemical Formula 8, i.e., 0<x<1.

In an example, x may satisfy 0.01≤x≤0.10, for example, 0.01≤x≤0.07, and for example, 0.01≤x≤0.05.

The poly(imide-amide) copolymer may have excellent optical and thermal properties, as well as a drastically decreased CTE.

According to yet another embodiment, provided is an article including the poly(imide-amide) copolymer.

In an embodiment, the article may be a film, a fiber, a coating material, or an adhesive.

The article may have a total light transmittance of greater than or equal to about 85%, in a wavelength range of 360 nanometers to 740 nanometers, the article may have light transmittance of greater than or equal to about 80% in a wavelength of 430 nanometers, and the article may have light transmittance of greater than or equal to about 50% in a wavelength of 400 nanometers.

The article may have a yellowness index ("YI") of less than or equal to about 5, for example, less than or equal to about 4.

The article may have a haze of less than or equal to about 0.5.

The article may have a birefringence of less than or equal to about 0.10, for example, less than or equal to about 0.093.

The article may have a coefficient of thermal expansion ("CTE") of less than or equal to about 10 parts per million per degree Centigrade ("ppm/° C."), for example, of less than or equal to about 7.5 ppm/° C., in a temperature range of 50° C. to 150° C.

The article may have a coefficient of thermal expansion ("CTE") of less than or equal to about 15 parts per million per degree Centigrade ("ppm/° C."), for example, of less than or equal to about 12.5 ppm/° C., in a temperature range of 50° C. to 250° C.

The article may have a coefficient of thermal expansion ("CTE") of less than or equal to about 20 parts per million per degree Centigrade ("ppm/° C."), for example, of less than or equal to about 18 ppm/° C., in a temperature range of 50° C. to 300° C.

The article may have a glass transition temperature ("Tg") of greater than or equal to about 300° C., for example, of greater than or equal to about 330° C.

The article may have a 1.0% weight degradation temperature ("Td(1.0%)") of greater than or equal to about 500° C.

The article may have a 5.0% weight degradation temperature ("Td(5.0%)") of greater than or equal to about 550° C.

According to still another embodiment, provided is a display device including the article.

The display device may be a liquid crystal device ("LCD"), an organic light emitting diode ("OLED") or a complementary metal-oxide semiconductor ("CMOS").

Hereafter, the technology of this disclosure is described in detail with reference to examples. The following examples and comparative examples are not restrictive but are illustrative.

EXAMPLES

Example 1

Synthesis of a New Diamine Monomer, DA168, Containing an Aramide Group Therein

A diamine monomer named as DA168' including an aramid structure therein is prepared by the following Reaction Scheme 2. First, TFDB and para-nitro benzoyl chloride are reacted to prepare a precursor compound, N,N'-(2,2'-bis(trifluoromethyl)-[1,1'-biphenyl]-4,4'-diyl)bis(4-nitrobenzamide) (named as "DA167"), and then the precursor compound, DA167 is reduced by using Zn (zinc) catalyst to prepare a final product, DA168.

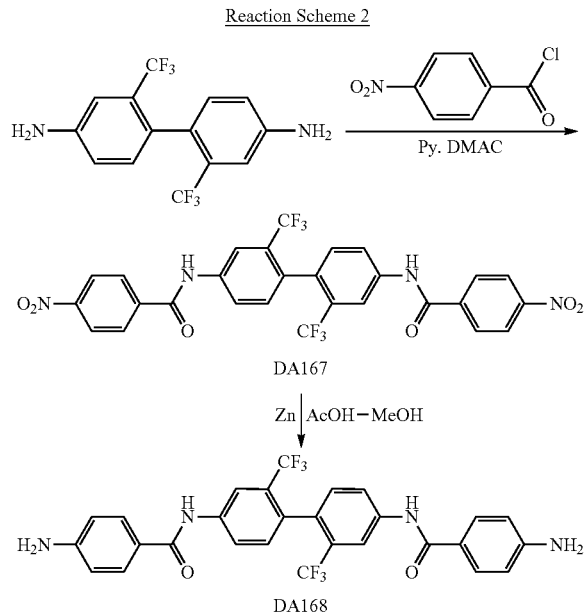

Reaction Scheme 2

Particularly, TFDB 64.048 g (0.2 mol) and pyridine 39.55 g (0.5 mol) are dissolved in DMAC (400 mL). The solution is stirred vigorously, and para-nitrobenzoyl chloride 81.651 g (0.44 mol) is added in small portions within 5 minutes. Solution becomes yellow and some heating occurs. The resulting solution is stirred and heated at 80° C. for additional 3 hours and i-PrOH (1.5 L) is added. Crystalline precipitate is filtered, washed with i-PrOH (3×100 mL), collected from filter and dissolved in DMAC (500 mL) at reflux, i-PrOH (1.5 L) is added to the hot DMAC solution causing precipitation of crystalline material. Solid is filtered, suspended in 500 mL of hot i-PrOH and filtered again. Drying at 80° C. for 12 hours affords slightly greenish crystalline dinitro-compound DA167 80.9 g (yield 65.4%). $^1$H NMR 300 MHz spectrum of DA167 is as follows:

$^1$H NMR 300 MHz (DMSO-d6, δ, ppm): 7.43 (d, J1,2=8.46 Hz, 2 H), 8.12 (dd, J1,2=8.46 Hz, J1,3=2.07 Hz, 2 H), 8.24 (d, J1,2=8.85 Hz, 4 H), 8.36 (d, J1,2=2.07 Hz, 2 H), 8.42 (d, J1,2=8.85 Hz, 4 H), 10.96 (br. s, 2 H), UV, λmax=300 nm (∈=1×10$^6$ L×mol$^{-1}$×cm$^{-1}$).

IR (v, cm$^{-1}$): 710, 833, 851, 1013, 1053, 1116, 1184, 1244, 1317, 1350, 1396, 1413, 1487, 1516, 1601, 1614, 1672.

FIGS. 1A and 1B are graphs of peak intensity versus chemical shift (parts per million, ppm) illustrating $^1$H NMR spectra of DA167. FIG. 1B is enlarged view of a part of FIG. 1A.

The prepared precursor, DA167, i.e., N,N'-(2,2'-bis(trifluoromethyl)-[1,1'-biphenyl]-4,4'-diyl)bis(4-nitrobenzamide) (6.18 g, 0.01 mol) is dissolved in the mixture of solvents EtOH/AcOH (100/20 mL) at mild reflux. Zinc (Zn) powder (6.54 g, 0.1 mol) is carefully added in 1 portion, which is extremely exothermic, thus 2 liter (L) high-beaker is recommended to be used. The mixture is immediately bubbled up within several seconds, and then clear colorless solution is formed. The mixture is refluxed for additional 10 minutes or more and filtered hot to remove unreacted zinc. The solution is poured into H$_2$O (300 mL), resulting in white precipitate. Precipitate is filtered and thoroughly washed with H$_2$O (2×300 mL) by suspension-filtration procedure to remove traces of mother liquor and zinc salts. Filtration of solid and drying under vacuum at 90° C. for 12 hours yields white powder of N,N'-(2,2'-bis(trifluoromethyl)-[1,1'-biphenyl]-4,4'-diyl)bis(4-aminobenzamide), DA168 4.1 g (yield 73.5%). $^1$H NMR 300 MHz of DA168 are as follows:

$^1$H NMR 300 MHz (DMSO-d6, δ, ppm): 5.86 (s, 4 H), 6.64 (d, J1,2=8.67 Hz, 4 H), 7.32 (d, J1,2=8.48 Hz, 2 H), 7.77 (d, J1,2=8.67 Hz, 4 H), 8.07 (dd, J1,2=8.48 Hz, J1,3=2.07 Hz, 2 H), 8.34 (d, J1,2=2.07 Hz, 2 H) 10.17 (br. s, 2 H).

$^{13}$C NMR 75 MHz (DMSO-d6, δ, ppm): 112.7, 116.9, 120.5, 122.2, 125.8, 129.7, 130.8, 132.4, 140.1, 152.6, 165.8. UV-vis, λmax=318 nm (∈=7×10$^4$ L×mol$^{-1}$×cm$^{-1}$).

IR (v, cm$^{-1}$): 758, 835, 883, 903, 928, 959, 1001, 1051, 1072, 1107, 1134, 1163, 1248, 1296, 1412, 1487, 1508, 1530, 1585, 1607, 1618, 1649, 3281, 3412.

FIGS. 2A and 2B are graphs of peak intensity versus chemical shift (parts per million, ppm) illustrating $^1$H NMR spectra of DA168. FIG. 2B is enlarged view of a part of FIG. 2A.

FIG. 3 shows graphs of ultra violet absorption of DA168 and DA167.

Example 2

Synthesis of Poly(Imide-amide) Copolymers

A stirrer is placed in a 20 mL vial, and 14.9 mL of DMAC is loaded as a polymerization solvent, after which 0.0238 g (0.0426 mmol) of DA168 prepared in Example 1, 1.3511 g (4.219 mmol) of TFDB, and 1 drop of acetic acid are added thereto. The mixture is stirred with a magnet stirrer while loading 1.2538 g (4.261 mmol) of BPDA, and the reaction is conducted at 25° C. for 48 hours. From the reaction, a poly(imide-amide) copolymer including about 1 mol % of DA168 based on the total diamine content is obtained.

The above reaction is repeated to poly(imide-amide) copolymers including using different content of DA168 based on the total content of diamine as shown in Table 1 below. Also, as a comparison, a poly(imide-amide) copolymer prepared by reacting TFDB and BPDA at a mole ratio of 1:1, without using DA168.

Example 3

Preparation of Poly(Imide-amide) Copolymer Films and Evaluation of the Properties of the Films Poly(imide-amide) films are prepared by using poly (imide-amide) copolymers having different content of DA168, prepared in Examples 2. The films are prepared by coating the poly(imide-amide) copolymer solutions onto a glass plate, predrying at 70° C. for 40 min, gradually heating from 20° C. to 300° C. for 90 minutes, and keeping for 60 minutes at 300° C. The properties of the films prepared are summarized in Table 1.

TABLE 1

| DA168 Content | Δ, μM | YI | haze | Y | T (%) 400 nm | T (%) 430 nm | CTE (ppm/° C.) 50~150 | CTE (ppm/° C.) 50~250 | CTE (ppm/° C.) 50~300 | $T_g$, ° C. | $T_d$ (° C.) 0.1% | $T_d$ (° C.) 1% | $T_d$ (° C.) 5% | Δn |
|---|---|---|---|---|---|---|---|---|---|---|---|---|---|---|
| 0 mol % | 10 | 2.25 | 0.38 | 87.51 | 54.55 | 85.16 | 19.53 | 26.53 | 38.4 | 342 | 325 | 523 | 572 | 0.0744 |
| 1 mol % | 10 | 2.42 | 0.32 | 87.38 | 54.31 | 84.93 | 7.69 | 12.22 | 17.42 | 340 | 399 | 524 | 570 | 0.0803 |
| 3 mol % | 10 | 2.65 | 0.21 | 87.33 | 53.03 | 84.62 | 5.24 | 8.97 | 15.47 | 342 | 392 | 520 | 569 | 0.0871 |
| 5 mol % | 10 | 3.04 | 0.45 | 87.21 | 52.31 | 84.28 | 4.5 | 8.11 | 14.61 | 341 | 403 | 518 | 570 | 0.089 |
| 10 mol % | 10 | 3.55 | 0.62 | 87.13 | 50.06 | 83.39 | 4.08 | 7.43 | 12.74 | 341 | 409 | 509 | 563 | 0.0922 |
| 15 mol % | 10 | 3.96 | 0.20 | 86.89 | 49.45 | 83.38 | 4.11 | 7.29 | 12.13 | 340 | 390 | 502 | 556 | 0.0939 |
| 20 mol % | 10 | 4.64 | 0.45 | 86.82 | 47.63 | 82.54 | 3.51 | 6.78 | 10.97 | 339 | 398 | 494 | 549 | 0.0968 |
| 30 mol % | 10 | 5.47 | 0.35 | 86.32 | 43.11 | 80.53 | 3.37 | 6.24 | 9.93 | 340 | 394 | 485 | 539 | 0.1001 |
| 40 mol % | 10 | 6.74 | 0.64 | 86.13 | 41.15 | 80.22 | 2.66 | 5.16 | 8.35 | 340 | 384 | 478 | 530 | 0.1047 |
| 50 mol % | 10 | 7.93 | 0.23 | 85.97 | 36.69 | 77.37 | 2.48 | 4.59 | 7.44 | 338 | 376 | 477 | 527 | 0.1085 |
| 100 mol % | 10 | 14.02 | 0.32 | 83.84 | 23.36 | 72.53 | −0.32 | 1.04 | 3.03 | 334 | 364 | 464 | 519 | 0.1309 |

As shown from Table 1, only 1 mol % of DA168 can drastically decrease a CTE of the films prepared using the same in all temperature ranges compared to the films that do not include DA168. Further, all content range of DA168 can decrease CTE of the films prepared by using the same, compared to the films that do not include DA168.

Meanwhile, as DA168 content increases to a certain point, the thermal properties, such as glass transition temperature, weight lost temperature, and the like, and the optical properties, such as transmittance, yellowness index, and the like, maintain as the films that do not contain DA168.

That is, the new diamine compound according to an embodiment, DA168, can drastically decrease a CTE of the poly(imide-amide) films including the same, while not deteriorating basic properties of the poly(imide-amide) films that do not include the same, such as optical and thermal properties, and thus can be advantageously used in various field where a low CTE is desired.

FIGS. 4 to 8 shows graphs of transmittance at different wavelengths, yellowness index ("YI"), birefringence ("Δ"), coefficient of thermal expansion ("CTE") (parts per million per degree Centigrade, ppm/° C.), glass transition temperature ("Tg"), and 1% weight degradation temperatures and 5% weight degradation temperature, of poly(imide-amide) films versus DA168 content (%) of the films.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A poly(imide-amide) copolymer reaction product of a diamine comprising a diamine represented by Chemical Formula 1 and a dianhydride represented by Chemical Formula 5:

Chemical Formula 1

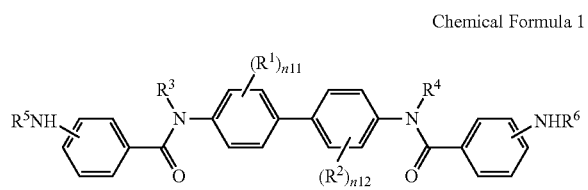

wherein in Chemical Formula 1,
R$^1$ and R$^2$ are the same or different, and are each independently an electron-withdrawing group,
R$^3$ to R$^6$ are the same or different, and are each independently selected from a hydrogen, a substituted or unsubstituted C1 to C20 alkyl group, and a substituted or unsubstituted C6 to C20 aryl group, and
n11 and n12 are the same or different, and are each independently an integer from 1 to 4;

Chemical Formula 5

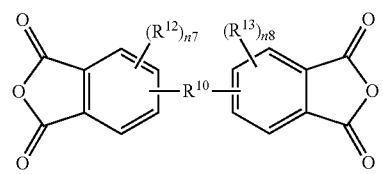

wherein in Chemical Formula 5,
R$^{10}$ is a substituted or unsubstituted C1 to C30 aliphatic group, a substituted or unsubstituted C3 to C30 alicyclic organic group, a substituted or unsubstituted C6 to C30 aromatic organic group, or a substituted or unsubstituted C2 to C30 heterocyclic group,
R$^{12}$ and R$^{13}$ are the same or different and are each independently a halogen, a hydroxyl group, a substituted or unsubstituted C1 to C10 aliphatic group, a substituted or unsubstituted C6 to C20 aromatic group, an alkoxy group of formula —OR$^{205}$, wherein R$^{205}$ is a C1 to C10 aliphatic organic group, or a silyl group of formula —SiR$^{209}$R$^{210}$R$^{211}$, wherein R$^{209}$, R$^{210}$, and R$^{211}$ are the same or different and are each independently a hydrogen or a C1 to C10 aliphatic organic group, and n7 and n8 are the same or different and are each independently an integer ranging from 0 to 3.

2. The poly(imide-amide) copolymer according to claim 1, wherein in Chemical Formula 1, R$^1$ and R$^2$ are the same or different, and are each independently —CF$_3$, —CCl$_3$, —CBr$_3$, —Cl$_3$, —C$_2$F$_5$, —C$_3$F$_7$, —COOH, —COOMe, —COOEt, —OMe, —OEt, —SF$_6$, —F, —Cl, or —Br.

3. The poly(imide-amide) copolymer according to claim 1, both R$^1$ and R$^2$ are —CF$_3$, and all of R$^3$ to R$^6$ are hydrogens.

4. The poly(imide-amide) copolymer according to claim 1, wherein the dianhydride represented by Chemical Formula 5 comprises at least one of a dianhydride represented by Chemical Formula 6 and Chemical Formula 7:

Chemical Formula 6

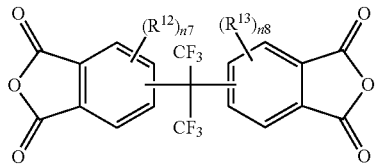

Chemical Formula 7

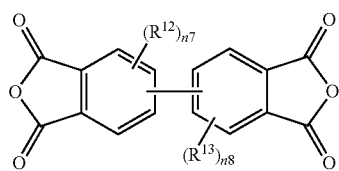

wherein in Chemical Formulae 6 and 7,

R$^{12}$ and R$^{13}$ are the same or different, and are independently a halogen, a hydroxy group, a substituted or unsubstituted C1 to C10 aliphatic organic group, a C6 to C20 aromatic organic group, an alkoxy group of formula —OR$^{208}$, wherein R$^{208}$ is a C1 to C10 aliphatic organic group, or a silyl group of formula —SiR$^{209}$R$^{210}$R$^{211}$, wherein R$^{209}$, R$^{210}$, and R$^{211}$ are the same or different, and are each independently hydrogen or a C1 to C10 aliphatic organic group, and n7 and n8 are each independently integers ranging from 0 to 3.

5. The poly(imide-amide) copolymer according to claim 1, wherein the diamine further comprises at least one selected from a compound represented by Chemical Formula 2, a compound represented by Chemical Formula 3, and a compound represented by Chemical Formula 4:

Chemical Formula 2

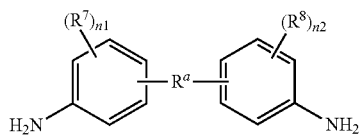

wherein in Chemical Formula 2,

R$^a$ is a substituted or unsubstituted C3 to C30 alicyclic organic group, a substituted or unsubstituted C6 to C30 aromatic organic group, or a substituted or unsubstituted C2 to C30 heterocyclic group, or a substituted or unsubstituted C13 to C20 fluorenylene group, R$^7$ and R$^8$ are the same or different and are each independently a halogen, a hydroxyl group, a substituted or unsubstituted C1 to C10 aliphatic group, a substituted or unsubstituted C6 to C20 aromatic group, an alkoxy group of formula —OR$^{200}$, wherein R$^{200}$ is a C1 to C10 aliphatic organic group, or a silyl group of formula —SiR$^{201}$R$^{202}$R$^{203}$, wherein R$^{201}$, R$^{202}$, and R$^{203}$ are the same or different and are each independently a hydrogen or a C1 to C10 aliphatic organic group, and n1 and n2 are the same or different and are each independently an integer ranging from 0 to 4;

Chemical Formula 3

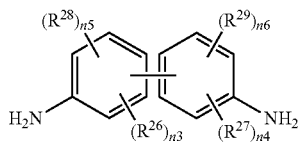

wherein in Chemical Formula 3,

R$^{26}$ and R$^{27}$ are the same or different and are each independently an electron withdrawing group, R$^{28}$ and R$^{29}$ are the same or different, and are each independently a halogen, a hydroxy group, a substituted or unsubstituted C1 to C10 aliphatic organic group, a substituted or unsubstituted C6 to C20 aromatic organic group, an alkoxy group of formula —OR$^{204}$, wherein R$^{204}$ is a C1 to C10 aliphatic organic group, or a silyl group of formula —SiR$^{205}$R$^{206}$R$^{207}$, wherein R$^{205}$, R$^{206}$, and R$^{207}$ are the same or different, and are each independently a hydrogen or a C1 to C10 aliphatic organic group, n3 is an integer ranging from 1 to 4, n5 is an integer ranging from 0 to 3, provided that n3+n5 is an integer ranging from 1 to 4, n4 is an integer ranging from 1 to 4, and n6 is an integer ranging from 0 to 3, provided that n4+n6 is an integer ranging from 1 to 4;

Chemical Formula 4

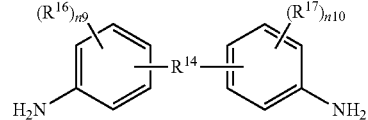

wherein in Chemical Formula 4,

R$^{14}$ is —O—, —S—, —C(=O)—, —CH(OH)—, —S(=O)$_2$—, —Si(CH$_3$)$_2$—, —(CH$_2$)$_p$—, wherein 1≤p≤10, —(CF$_2$)$_q$—, wherein 1≤q≤10, —C(CH$_3$)$_2$—, —C(CF$_3$)$_2$—, and —C(=O)NH—, or a substituted or unsubstituted C6 to C30 aromatic organic group, wherein the aromatic organic group comprises one aromatic ring, two or more aromatic rings fused together to provide a condensed ring system, or two or more moieties linked through a single bond or through a functional group selected from a fluorenylene group, —O—, —S—, —C(=O)—, —CH(OH)—, —S(=O)$_2$—, —Si(CH$_3$)$_2$—, —(CH$_2$)$_p$— wherein 1≤p≤10, —(CF$_2$)$_q$—, wherein 1≤q≤10, —C(CH$_3$)$_2$—, —C(CF$_3$)$_2$—, and —C(=O)NH—, $R^{16}$ and $R^{17}$ are the same or different, and are each independently a halogen, a hydroxy group, a substituted or unsubstituted C1 to C10 aliphatic organic group, a substituted or unsubstituted C6 to C20 aromatic organic group, an alkoxy group of formula —$OR^{212}$, wherein $R^{212}$ is a C1 to C10 aliphatic organic group, or a silyl group of formula —$SiR^{213}R^{214}R^{215}$, wherein $R^{213}$, $R^{214}$, and $R^{215}$ are the same or different, and are each independently a hydrogen or a C1 to C10 aliphatic organic group, and n9 and n10 are each independently an integer ranging from 0 to 4.

6. The poly(imide-amide) copolymer according to claim 5, wherein in Chemical Formula 2, $R^a$ is selected from chemical formulae:

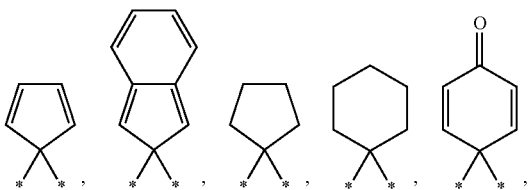

-continued

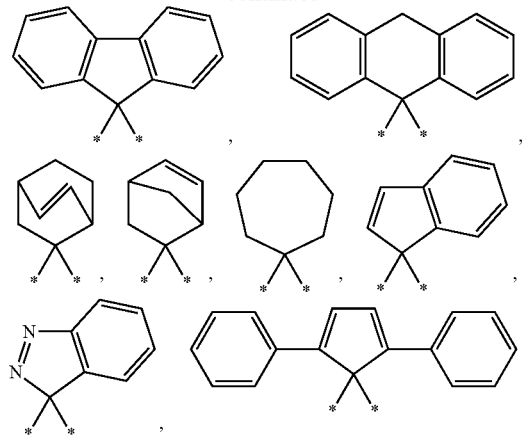

7. The poly(imide-amide) copolymer according to claim 5, wherein in Chemical Formula 3, $R^{26}$ and $R^{27}$ are the same or different, and are each independently selected from —$CF_3$, —$CCl_3$, —$CBr_3$, —$Cl_3$, —$NO_2$, —CN, —C(=O)$CH_3$, and —$CO_2C_2H_5$.

8. The poly(imide-amide) copolymer according to claim 5, wherein in Chemical Formula 4, $R^{14}$ is $SO_2$, and both n9 and n10 are the integer of 0.

* * * * *